US010900101B2

(12) United States Patent
Park

(10) Patent No.: US 10,900,101 B2
(45) Date of Patent: Jan. 26, 2021

(54) COPPER ALLOY FOR DENTAL PROSTHESIS

(71) Applicant: Dong Han Park, Busan (KR)

(72) Inventor: Dong Han Park, Busan (KR)

( * ) Notice: Subject to any disclaimer, the term of this patent is extended or adjusted under 35 U.S.C. 154(b) by 0 days.

(21) Appl. No.: 16/640,700

(22) PCT Filed: Jul. 31, 2018

(86) PCT No.: PCT/KR2018/008656
§ 371 (c)(1),
(2) Date: Feb. 20, 2020

(87) PCT Pub. No.: WO2019/045285
PCT Pub. Date: Mar. 7, 2019

(65) Prior Publication Data
US 2020/0354814 A1  Nov. 12, 2020

(30) Foreign Application Priority Data
Aug. 31, 2017 (KR) .......................... 10-2017-0111056

(51) Int. Cl.
*C22C 9/01* (2006.01)
*A61K 6/847* (2020.01)
(52) U.S. Cl.
CPC ................ *C22C 9/01* (2013.01); *A61K 6/847* (2020.01)
(58) Field of Classification Search
None
See application file for complete search history.

(56) References Cited

U.S. PATENT DOCUMENTS

| | | | |
|---|---|---|---|
| 4,786,470 A | 11/1988 | Benetti et al. | |
| 7,128,871 B2 * | 10/2006 | Davitz | ...................... C22C 5/08 420/504 |
| 2011/0129383 A1 * | 6/2011 | Yang-Tung | ............... C22C 9/04 420/471 |

FOREIGN PATENT DOCUMENTS

| | | |
|---|---|---|
| JP | H11-106851 A | 4/1999 |
| JP | 2001-220629 A | 8/2001 |
| JP | 2004-143574 A | 5/2004 |
| KR | 10-2007-0099496 A | 10/2007 |
| KR | 10-1133677 A | 4/2012 |
| KR | 10-2014-0116989 A | 10/2014 |
| KR | 10-1480611 B1 | 1/2015 |
| KR | 10-1829711 B1 | 2/2018 |

OTHER PUBLICATIONS

Eschler, P. Y. et al., "Copper-aluminum bronze—a substitute material for gold dental alloy?" European Cells and Materials, vol. 5, Suppl. 1, pp. 49-50 (2003).
KR Grant of Patent dated Jan. 6, 2018 as received in Application No. 10-2017-0111056.

* cited by examiner

*Primary Examiner* — Brian D Walck
(74) *Attorney, Agent, or Firm* — Maschoff Brennan

(57) ABSTRACT

The present invention relates to a copper alloy for dental prosthesis and specifically, to a copper alloy for dental prosthesis having such color and luster that the copper alloy can be used as a substitute for a gold alloy and having excellent resistance to corrosion, wherein the copper alloy comprises, in wt %, 7-10% of Al, 1-2.5% of In, 1-2.5% of Sn, 2-4% of Fe, 2-3.5% of Ni, 2.5-4% of Mn, 2-5% of Zn, and the balance Cu.

1 Claim, 2 Drawing Sheets

[Fig. 1]
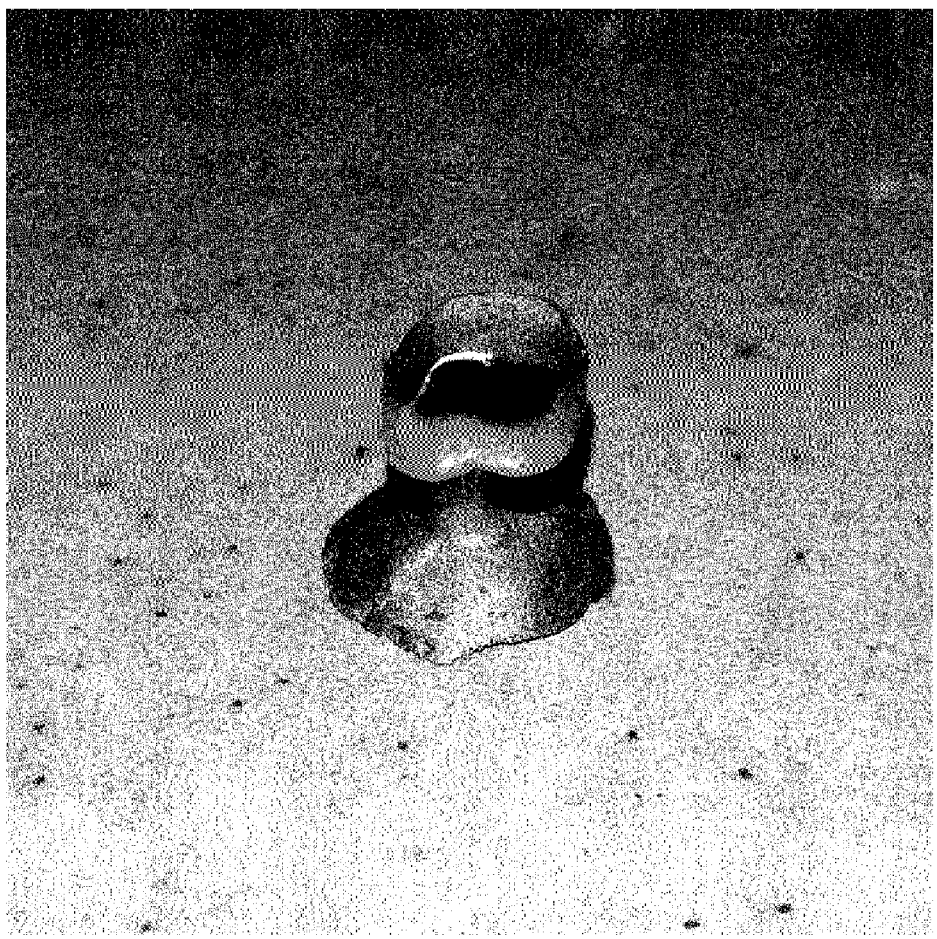

[Fig. 2]
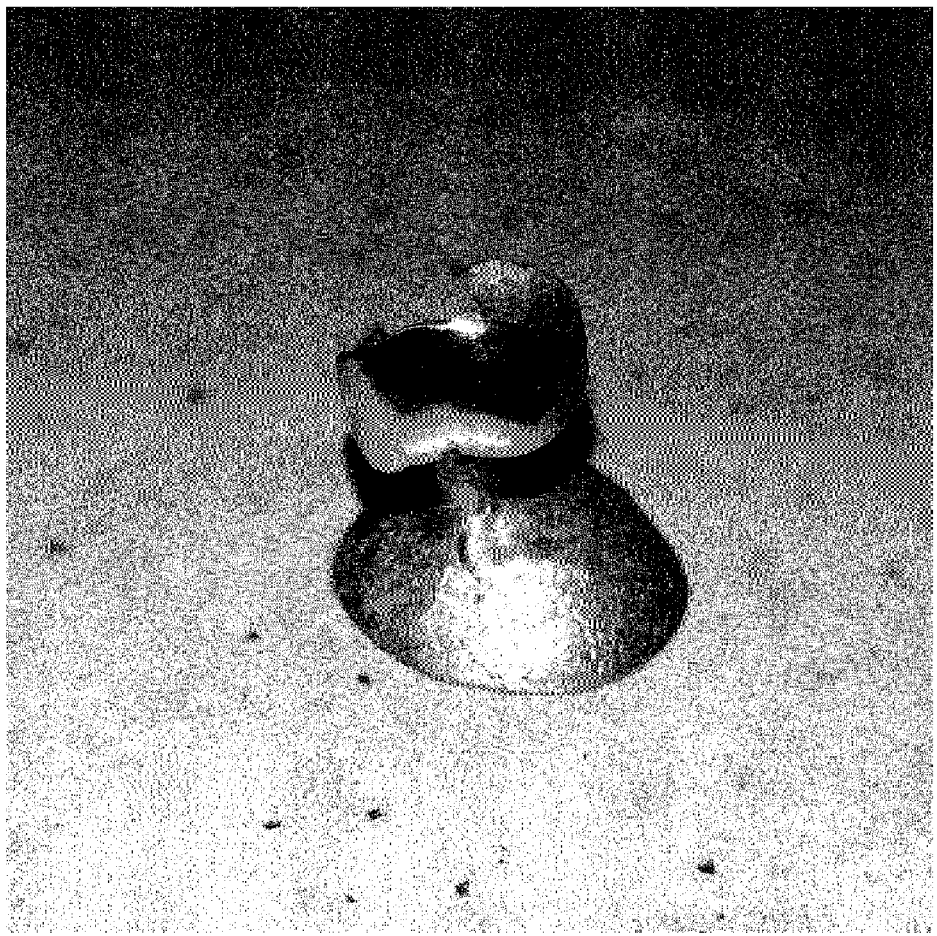

COPPER ALLOY FOR DENTAL PROSTHESIS

TECHNICAL FIELD

The present invention relates to a copper alloy for dental prosthesis, and more particularly to a copper alloy for dental prosthesis having such color and luster that the copper alloy may be used as a substitute for a gold alloy and having excellent resistance to corrosion.

BACKGROUND ART

A noble metal alloy and a non-noble metal alloy are used as an alloy for dental prosthesis. A gold alloy, which includes gold (Au) as a main component, is frequently used as the noble metal alloy.

Gold (Au) has good biocompatibility, but pure gold itself is too soft and weak to be used for dental purposes and thus is used in such a way that gold is alloyed with other metals.

The gold alloy has high corrosion resistance in the oral cavity, long-lasting luster, high casting precision, excellent strength, ductility, etc., and especially high fracture resistance at the corners. The gold alloy is often used together with platinum (Pt), silver (Ag), palladium (Pd), etc. In addition, copper (Cu), iron (Fe), tin (Sn), etc. are contained in a small amount to ensure strength, hardness, ductility and malleability suitable for withstanding the occlusal force in the oral cavity.

As an example, there is the gold alloy disclosed in Korean Registered Patent No. 10-1133677, in which a small amount of titanium may be added into the gold alloy to refine a metal structure. As shown in this prior art, the noble metal alloy is so configured that the composition ratio of gold (Au), silver (Ag), platinum (Pt) and palladium (Pd) corresponding to the noble metal is 92.9 to 96.85 wt %, and thus the price thereof is inevitably expensive due to the very high proportion of noble metals therein.

To replace such expensive noble metal alloy, a nickel-chromium (Ni—Cr) alloy is used as a non-noble metal alloy, in that the Ni—Cr alloy has a light weight and a less feeling of irritation. However, the color thereof is so close to white (platinum color) that users are often reluctant to use this alloy.

Copper (Cu) has an advantage of being close to a (golden) yellow color, rich in malleability, easy to process, easy to melt down at a melting point as low as 1083° C., and inexpensive. However, copper has a lack of strength, poor castability and very low corrosion resistance. For example, if being oxidized in the oral cavity, discoloration, etc. occurs to the copper.

Out of copper alloys, a copper-zinc (Cu—Zn) alloy, that is, a brass-based alloy, is known to have an increase in strength by zinc and have excellent castability. In case of adding 30-35 wt % of zinc, the Cu—Zn alloy turns into a golden color and its melting temperature becomes low. However, there is a problem that the Cu—Zn alloy has low resistance to corrosion and discoloration and has high casting shrinkage.

In addition, a copper-aluminum (Cu—Al) alloy is also used a lot. In case of using 5-12 wt % of aluminum, the Cu—Al alloy turns into a golden color and its acid and alkali corrosion resistance becomes high.

There have been many ongoing studies on adjusting various components of the copper alloy and a ratio thereof to achieve similar properties to those of the gold alloy. As one example, an attempt has been made to develop a (golden) yellow-colored copper alloy having copper as a main component as shown in Korean Registered Patent No. 10-1480611. However, it is difficult to lower down manufacturing costs because this copper alloy still requires some palladium, i.e., a noble metal.

Even in case of a copper alloy for dental prosthesis, which has come into the market, like NPG of Aalbadent Inc., USA, there is a problem that this copper alloy has such weak resistance to corrosion that discoloration or rust occurs thereto.

DETAILED DESCRIPTION OF THE INVENTION

Technical Problem

An object of the present invention, which is applied in order to solve the aforementioned problems of the prior art, is to provide a copper alloy which shows a color similar to that of a gold alloy without the addition of an expensive noble metal and also has strong resistance to corrosion and discoloration.

Technical Solution

A copper alloy for dental prosthesis of the present invention includes, in wt %, 7-10% of Al, 1-2.5% of In, 1-2.5% of Sn, 2-4% of Fe, 2-3.5% of Ni, 2.5-4% of Mn, 2-5% of Zn and the balance of Cu.

Advantageous Effects of the Invention

According to the present invention, there is provided a copper alloy for dental prosthesis which has a (golden) yellow color without the addition of a noble metal and also has strong resistance to corrosion, thus having an effect of reducing manufacturing costs.

DESCRIPTION OF THE DRAWINGS

FIG. 1 is a photographic view of a specimen according to one example of the present invention.

FIG. 2 is a photographic view of a specimen according to a comparative example.

BEST MODE

The present invention relates to a copper alloy for dental prosthesis which is manufactured by using copper as a main component and adding aluminum, indium, tin, iron, nickel, manganese and zinc therein as an essential composition, and details thereof are as follows.

If aluminum (Al) is added in an amount of 7 wt % or less, an alloy for dental prosthesis does not turn into a golden color. If Al is added in an amount of 10 wt % or more, the alloy for dental prosthesis turns into a white color. Indium represents the highest fluidity of casting in the range of 1-2.5 wt % and has corrosion resistance which decreases at the upper limit or more.

If tin (Sn) used to improve corrosion resistance is added in an amount of 1 wt % or less, an addition effect thereof is not obtained. If Sn is added in an amount of 2.5 wt % or more, and the ductility of the alloy is decreased. If iron (Fe) is added in an amount of 2 wt % or less, the strength of alloy for dental prosthesis becomes too low to use. If Fe is added in an amount of 4 wt % or more, the hardness of alloy for dental prosthesis is increased, thereby causing an unpleasant feeling during mastication.

If nickel (Ni) is added in an amount of 2 wt % or less, fluidity is decreased. When nickel (Ni) is added in an amount of 3.5 wt % or more, elasticity is decreased. Further, if manganese (Mn) is added in an amount of 2.5 wt % or less, an evaporation point is lowered, thereby causing a phenomenon in which a molten metal is burned while boiling. When manganese (Mn) is added in an amount of more than 4 wt %, an alloy for dental prosthesis becomes brittle.

Zinc (Zn) is used in an amount of 2-5 wt %. At the lower limit or less of Zn, fluidity is decreased so that castability may deteriorate. At the upper limit or more of Zn, hardness and strength are decreased and the alloy turns into a red color.

Each of the components at the ratio as above is subject into a melting process as follows. First, the components were stacked into a melting pot in the order of copper—(iron/nickel/manganese)—copper from the bottom thereof, then heated to about 1400° C. to melt down those components as a whole. After confirming that all of them were melt down thoroughly, heating was stopped, after which aluminum/tin/indium/zinc were put thereinto and heated to 1200° C. again. At that time, if a heating temperature is high, gas may be generated so that it is necessary to carefully control the temperature. Once it is confirmed that melting is completed, the resulting molten metal is poured into a mold having a desired shape to be manufactured into a shape of an ingot, a rod, etc., or may be subject to the rolling process to be manufactured into a board, if necessary.

Hereinafter, the present invention will be described in detail through examples.

Example

A copper alloy for dental prosthesis was manufactured with a composition of alloy as shown in the following Table 1, and then a specimen was manufactured into a crown shape as shown in FIG. 1. FIG. 1 shows a picture of a crown-shaped specimen manufactured with a composition as shown in Example 2.

TABLE 1

Composition ratio (wt %) of the inventive alloys according to examples

|  | Cu | Al | In | Sn | Fe | Ni | Mn | Zn |
|---|---|---|---|---|---|---|---|---|
| Example 1 | 74.3 | 8.9 | 2.0 | 1.8 | 3.5 | 3.0 | 2.5 | 4 |
| Example 2 | 76.8 | 7.8 | 1.9 | 2.0 | 2.9 | 2.9 | 2.8 | 2.9 |

Comparative Example

A copper alloy for dental prosthesis by Aalbadent Inc., USA, which has come into the market, was used as Comparative Example, and the components thereof are as shown in Table 2. As Comparative Example, a specimen was also manufactured into a crown shape as shown in FIG. 2.

TABLE 2

Composition ratio (wt %) of the alloy according to comparative example

|  | Cu | Al | Fe | Ni | Mn | Zn |
|---|---|---|---|---|---|---|
| Comparative Example | 80.7 | 7.8 | 2.9 | 4.3 | 2.3 | 2.0 |

<Color Comparison>

When comparing FIG. 1 and FIG. 2 with each other, in which the inventive specimen of Example 2 and the specimen of Comparative Example were photographed at the same place and under the same illumination, it may be seen that the specimen of the present invention shows a color close to the golden color. Thus, it may be also seen that the color of the present invention is extremely similar to that of the product which is available in the market as a substitute alloy for gold.

<Corrosion Resistance>

The results of testing corrosion resistance with regard to five specimens of Examples 1 and 2 and five specimens of Comparative Example are as shown in Table 3.

A method for testing corrosion resistance is as follows. After preparing a solution in which 22.3±0.1 g of 35% sodium sulfide (Na2S) was dissolved in 1000±3 ml of distilled water, the process of immersing the specimen in the solution for 10-15 seconds per minute was repeated for 72 hours. The solution was exchanged every 24 hours. When exchanging the solution, it was determined by visual observation whether there is any corrosion and discoloration.

If rust was observed by the visual observation, it was determined that corrosion occurred, and if a change in color was observed, it was determined that discoloration occurred.

The specimen of Comparative Example did not show any occurrence of rust even in 72 hours later, but it was observed that three specimens are discolored in the form of a golden color mixed with a slightly reddish tint. In contrast, it was observed that one specimen is discolored in the specimen of Example 1 out of all the specimens of Examples of the present invention. In the specimen of Example 2, rust and discoloration did not occur. Thus, it was determined that the alloy of the present invention has an excellent effect of corrosion resistance compared to the commercial alloy of Comparative Example.

TABLE 3

Results of an experiment on corrosion resistance

|  | Rust occurrence | | | Discoloration | | |
|---|---|---|---|---|---|---|
|  | In 24 hours later | In 48 hours later | In 72 hours later | In 24 hours later | In 48 hours later | In 72 hours later |
| Example 1 | None | None | None | None | None | One discolored |
| Example 2 | None | None | None | None | None | None |
| Comparative Example | None | None | None | None | None | Three discolored |

INDUSTRIAL APPLICABILITY

The present invention can be applied to a copper alloy having a color and luster similar to those of gold and having excellent resistance to corrosion, and the copper alloy of the present invention can be used as a material for dental prosthesis.

The invention claimed is:
1. A copper alloy for dental prosthesis, wherein the copper alloy includes, in wt %, 7-10% of Al, 1-2.5% of In, 1-2.5% of Sn, 2-4% of Fe, 2-3.5% of Ni, 2.5-4% of Mn, 2-5% of Zn and the balance of Cu.

* * * * *